(12) United States Patent
Ambady et al.

(10) Patent No.: US 11,679,121 B2
(45) Date of Patent: *Jun. 20, 2023

(54) MORPHOLINO OLIGONUCLEOTIDES USEFUL IN CANCER TREATMENT

(71) Applicants: United States Government As Represented By The Department of Veterans Affairs, Washington, DC (US); Oregon Health & Science University, Portland, OR (US)

(72) Inventors: Prakash Ambady, Portland, OR (US); Jeffrey Wu, Portland, OR (US); Edward Neuwelt, Portland, OR (US)

(73) Assignees: United States Government As Represented By The Department of Veterans Affairs, Washington, DC (US); Oregon Health & Science University, Portland, OR (US)

( * ) Notice: Subject to any disclaimer, the term of this patent is extended or adjusted under 35 U.S.C. 154(b) by 234 days.

This patent is subject to a terminal disclaimer.

(21) Appl. No.: 17/113,773

(22) Filed: Dec. 7, 2020

(65) Prior Publication Data

US 2021/0106608 A1    Apr. 15, 2021

Related U.S. Application Data

(63) Continuation of application No. 16/522,381, filed on Jul. 25, 2019, now Pat. No. 10,857,174.

(60) Provisional application No. 62/711,349, filed on Jul. 27, 2018.

(51) Int. Cl.
| C07H 21/04 | (2006.01) |
| A61K 31/711 | (2006.01) |
| A61K 9/00 | (2006.01) |
| A61P 35/00 | (2006.01) |
| A61K 31/4162 | (2006.01) |

(52) U.S. Cl.
CPC .......... *A61K 31/711* (2013.01); *A61K 9/0019* (2013.01); *A61P 35/00* (2018.01); *A61K 31/4162* (2013.01)

(58) Field of Classification Search
None
See application file for complete search history.

(56) References Cited

U.S. PATENT DOCUMENTS

| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,698,685 A | 12/1997 | Summerton et al. |
| 5,998,203 A | 12/1999 | Matulic-Adamic et al. |
| 6,753,423 B1 | 6/2004 | Cook et al. |
| 2003/0130186 A1 | 7/2003 | Vargeese et al. |
| 2004/0110296 A1 | 6/2004 | Vargeese et al. |
| 2004/0167090 A1 | 8/2004 | Monahan et al. |
| 2004/0192626 A1 | 9/2004 | McSwiggen et al. |
| 2004/0249178 A1 | 12/2004 | Vargeese et al. |
| 2005/0043219 A1 | 2/2005 | Manoharan et al. |
| 2005/0074771 A1 | 4/2005 | Cook et al. |
| 2005/0107325 A1 | 5/2005 | Manoharan et al. |
| 2005/0119470 A1 | 6/2005 | Manoharan et al. |
| 2005/0153337 A1 | 7/2005 | Manoharan |
| 2005/0158727 A1 | 7/2005 | Manoharan et al. |
| 2005/0239739 A1 | 10/2005 | Matulic-Adamic et al. |
| 2005/0282188 A1 | 12/2005 | Haeberli et al. |

FOREIGN PATENT DOCUMENTS

GB    2397818 B    3/2005

OTHER PUBLICATIONS

Agrawal S and Kandimalla ER,"Antisense therapeutics: is it as simple as complementary base recognition?", Mol Med today 6, 72-81 (2000).

Bocangel DB et al, "Multifaceted Resistance of Gliomas to Temozolomide1", Clin Cancer Res 8, 2725-2734 (2002).

Cirak S et al., "Exon skipping and dystrophin restoration in patients with Duchenne muscular dystrophy after systemic phosphorodiamidate morpholino oligomer treatment: an open-label, phase 2, dose-escalation study", Lancet 378, 595-605 (2011).

Delaney G et al, "The role of radiotherapy in cancer treatment: estimating optimal utilization from a review of evidence-based clinical guidelines", Cancer 104, 1129-1137 (2005).

Esteller M and Herman JG, "Generating Mutations but Providing Chemosensitivity: The Role of O6-methylguanine DNA Methyltransferase in Human Cancer", Oncogene 23, 1-8 (2004).

Fletcher S et al,"Morpholino oligomer-mediated exon skipping averts the onset of dystrophic pathology in the mdx mouse", Mol Ther 15, 1587-1592 (2007).

Goder A et al., "Lipoic acid inhibits the DNA repair protein O6-methylguanine-DNA methyltransferase (MGMT) and triggers its depletion in colorectal cancer cells with concomitant autophagy induction", Carcinogenesis 36, 817-831 (2015).

(Continued)

*Primary Examiner* — Kimberly Chong
(74) *Attorney, Agent, or Firm* — Ballard Spahr LLP

(57) ABSTRACT

Disclosed are morpholino oligonucleotides that can be used to silence expression of MGMT, pharmaceutical compositions that include said morpholino oligonucleotides, and methods of using said morpholino oligonucleotides in the treatment of cancer, particularly methods that involve the use of radiation to deliver said morpholino oligonucleotides.

20 Claims, 5 Drawing Sheets

Specification includes a Sequence Listing.

(56) References Cited

OTHER PUBLICATIONS

Goemans NM et al., "Systemic administration of PRO051 in Duchenne's muscular dystrophy", N Engl J Med 365, 1513-1522 (2011).

Hegi ME et al., "MGMT gene silencing and benefit from temozolomide in glioblastoma", N Engl J Med 352, 997-1003 (2005).

Karran P, "Carcinogenesis 22, 1931-1937 (2001)", Carcinogenesis 22, 1931-1937 (2001).

Kato T et al, "Efficient delivery of liposome-mediated MGMT-siRNA reinforces the cytotoxity of temozolomide in GBM-initiating cells", Gene Ther 17, 1363-1371 (2010).

Kitange GJ et al, "Induction of MGMT expression is associated with temozolomide resistance in glioblastoma xenografts", Neuro Oncol 11, 281-291 (2009).

Koo T and Wood MJ, "Clinical Trials Using Antisense Oligonucleotides in Duchenne Muscular Dystrophy", Hum Gene Ther 24, 479-488 (2013) (Abstract).

Maier P et al, "Cellular Pathways in Response to Ionizing Radiation and Their Targetability for Tumor Radiosensitization", Int J Mol Sci 17, E102. doi: 10.3390/ijms17010102 (2016).

Morcos PA et al, "Vivo-Morpholinos: a non-peptide transporter delivers Morpholinos into a wide array of mouse tissues", Biotechniques 45, 613-618 (2008).

Ochs K et al, "Apoptosis Induced by DNA Damage O6-Methylguanine Is Bcl-2 and Caspase-9/3Regulated and Fas/Caspase-8 Independent", Cancer Res 5815-5824 (2000).

Qian J et al, "Ionizing Radiation-Induced Adenovirus Infection Is Mediated by Dynamin 2", Cancer Res 65, 5493-5497 (2005).

Stupp R et al, "Radiotherapy plus Concomitant and Adjuvant Temozolomide for Glioblastoma ", N Engl J Med 352, 987-996 (2005).

Tsujiuchi T et al, "Preclinical evaluation of an O6-methylguanine-DNA methyltransferase-siRNA/liposome complex administered by convection-enhanced delivery to rat and porcine brains", Am J Transl Res 6, 169-178 (2014).

Zhang M et al., "Ionizing radiation increases adenovirus uptake and improves transgene expression in intrahepatic colon cancer xenografts", Mol Ther 8, 21-28 (2003).

U.S. Appl. No. 62/711,349, filed Jul. 27, 2018, Prakash Ambady (US Department of Veterans Affairs).

U.S. Appl. No. 16/522,381 U.S. Pat. No. 10,857,174, filed Jul. 25, 2019 (Dec. 8, 2020), Prakash Ambady (US Department of Veterans Affairs).

MORPHOLINO OLIGONUCLEOTIDES USEFUL IN CANCER TREATMENT

CROSS REFERENCE TO RELATED APPLICATIONS

This application is a continuation of U.S. application Ser. No. 16/522,381 (now U.S. Pat. No. 10,857,174) filed on Jul. 25, 2019, and which claims the benefit of the filing date of U.S. Provisional Application 62/711,349, which was filed on Jul. 27, 2018. The content of these earlier filed applications is hereby incorporated by reference in their entirety.

INCORPORATION OF THE SEQUENCE LISTING

The present application contains a sequence listing submitted herewith as a text file named "37759_0131_U3 SL.text" which is 4,096 bytes in size, created on Dec. 4, 2020, and is herein incorporated by reference pursuant to 37 C.F.R. § 1.52(e)(5).

FIELD

Generally, the field involves medicinal compounds and pharmaceutical compositions. More specifically, the field involves oligonucleotide-based compounds useful in the treatment of cancer.

BACKGROUND

Glioblastoma is an aggressive primary brain tumor that holds a very poor prognosis even with aggressive resection and chemo-radiation (CRT). The enzyme O-6-methylguanine-DNA methyltransferase (MGMT) plays a major role in this resistance to chemoradiotherapy (CRT) (Hegi M E et al, J Clin Oncol 26, 4189-4199 (2008); Nakagawachi T et al, Oncogene 22, 8835-8844 (2003); and Zhang J et al, Curr Mol Pharmacol 5, 102-114 (2012); all of which are incorporated by reference herein). The cytotoxic effect of CRT is mediated by the methylation of 0-6 and N-7 positions of guanylic acid and the N-3 position of adenine resulting in a continuous cycle of DNA base mismatch with eventual DNA strand breaks that ultimately trigger apoptosis (Stupp R et al, N Engl J Med 352, 987-996 (2005); Tentori L and Graziani G, Curr Med Chem 16, 245-257 (2009); and Fu D et al, Nat Rev Cancer 12, 104-120 (2012); all of which are incorporated by reference herein). MGMT is a DNA repair enzyme coded by the MGMT gene located on chromosome 10q26, that allows tumor cells to restore DNA damaged by CRT. MGMT is epigenetically silenced in about 45% of glioblastoma by methylation of CpG islands in the promotor regions located predominantly near the 5' end of the gene (Hegi 2008 supra and Nakagawachi 2003 supra). Inactivation of the MGMT gene by promotor methylation enhances the susceptibility of tumor cells to the cytotoxic effects of radiation and alkylating agents such as temozolamide (Stupp 2005 supra). Thus, MGMT is a target for treatment of glioblastoma and many other solid tumors such as lung, breast and renal cell carcinoma (Zhang 2012 supra, Ingold B et al, PLoS One 4, e4775 (2009); and Fan C H et al, Cell Death Dis 4, e876 (2013); both of which are incorporated by reference herein).

Various strategies to inhibit MGMT including the use of dose dense temozolomide regiments, pseudo-substrates of MGMT such as such as $O^6$-benzylguanine, $O^6$-4-bromothenyl guanine, or other agents such as quinolone derivatives, s-adenosylmethionine, or S-adenosylhocysteine have been and are being evaluated but have resulted in significant toxicity and limited clinical success (Zhang 2012 supra and Alonso M M et al, Cancer Res 67, 11499-11504 (2007) and Chen H Y et al, Anticancer Res 30, 4187-4192 (2010); incorporated by reference herein). Other investigators have used oncolytic viruses and small-interfering RNA (siRNA) sequences complexed with liposomes to downregulate MGMT (Kato T et al, Gene Ther 17, 1363-1371 (2010) and Jiang H et al, Expert Rev Anticancer Ther 6, 1585-1592 (2006); incorporated by reference herein). Although showing some efficacy in preclinical models, these approaches also result in off-target effects, immunological and other toxicities. As with many such approaches, delivery of such agents to achieve clinically relevant intratumoral distribution remains challenging (Tsujiuchi T et al, Am J Transl Res 6, 169-178 (2014); and Wang J et al, AAPS J 12, 492-503 (2010); both of which are incorporated by reference herein).

SUMMARY

Disclosed are morpholino oligonucleotides comprising a sequence selected from SEQ ID NO: 1, SEQ ID NO: 2, or SEQ ID NO: 3. The disclosed morpholino oligonucleotides are no more than 30 subunits in length. In some aspects, the morpholino oligonucleotides are no more than 40 submits in length. In some aspects, the morpholino oligonucleotides are no more than 25 subunits in length. In still other examples, the morpholino oligonucleotides consist of the sequence of SEQ ID NO: 1, SEQ ID NO: 2, or SEQ ID NO: 3.

Also disclosed are pharmaceutical compositions comprising the disclosed morpholino oligonucleotides and a pharmaceutically acceptable carrier. Such pharmaceutical compositions can contain morpholino oligonucleotides comprising any of SEQ ID NO: 1, SEQ ID NO: 2, or SEQ ID NO: 3 either alone or in combination. In some aspects, the pharmaceutical compositions can comprise the morpholino oligonucleotide comprising SEQ ID NO: 2 and not SEQ ID NO: 1 and SEQ ID NO: 3, the morpholino oligonucleotide comprising SEQ ID NO: 3 and not SEQ ID NO: 1 and SEQ ID NO: 2, the morpholino oligonucleotides comprising SEQ ID NO: 1 and SEQ ID NO: 2 and not SEQ ID NO: 3, the morpholino oligonucleotides comprising SEQ ID NO: 1 and SEQ ID NO: 3 and not SEQ ID NO: 2, and the morpholino oligonucleotides comprising SEQ ID NO: 2 and SEQ ID NO: 3 and not SEQ ID NO: 1, or the morpholino oligonucleotides comprising SEQ ID NO: 1, SEQ ID NO: 2, and SEQ ID NO: 3. The pharmaceutical can be formulated in any applicable manner known in the art, including for intravenous administration.

Further disclosed are methods of treating a tumor in a subject, such as a tumor that is characterized by MGMT overexpression. The methods include administering systemically the disclosed pharmaceutical compositions to the subject and administering a dose of ionizing radiation to the subject, thereby treating the tumor. In some aspects, the methods further involve administering temozolamide to the subject. In some aspects, the method involves determining that the tumor overexpresses MGMT. Any method of determining that the tumor overexpresses MGMT can be employed including measuring the expression of MGMT protein or determining the resistance to temozolamide of a sample of cells obtained from the tumor. In some aspects the dose of radiation is at least 1 Gy. In some aspects, the dose is at least 5 Gy. In some aspects, the dose of radiation is administered prior to the administration of the disclosed pharmaceutical compositions including at least 24 hours before.

Disclosed are pharmaceutical compositions for use in treating a tumor characterized by overexpression of MGMT. For example, disclosed are pharmaceutical compositions for use in treating a tumor characterized by overexpression of MGMT comprising the disclosed morpholino oligonucleotides. In some aspects, the pharmaceutical compositions are formulated for intravenous administration.

Disclosed herein are methods of enhancing delivery of one or more morpholino oligonucleotide, the methods comprising: administering to a subject with cancer a therapeutically effective amount of radiation prior to administering a therapeutically effective amount of the one or more morpholino oligonucleotides disclosed herein, wherein the one or more morpholino oligonucleotides comprise a sequence selected from SEQ ID NO: 1, SEQ ID NO: 2, or SEQ ID NO: 3. In same aspects the the one or more morpholino oligonucleotides is no more than 40 subunits in length.

Disclosed herein are methods of enhancing the efficacy of temozolamide, the methods comprising administering a therapeutically effect amount of one or more of the morpholino oligonucleotides disclosed herein prior to administering a therapeutically effective amount of temozolamide, wherein the one or more morpholino oligonucleotides comprising a sequence selected from SEQ ID NO: 1, SEQ ID NO: 2, or SEQ ID NO: 3. In same aspects the the one or more morpholino oligonucleotides is no more than 40 subunits in length.

Disclosed herein are methods of inducing apoptosis, the methods comprising: contacting a population of cells with a composition comprising a one or more of the morpholino oligonucleotides disclosed herein. Disclosed herein are methods of inducing apoptosis, the methods comprising: contacting a population of cells with a composition comprising a one or more of the morpholino oligonucleotides comprising the sequence of SEQ ID NO: 1, SEQ ID NO: 2, or SEQ ID NO: 3, wherein the contacting of the cells with the composition induces apoptosis of the cells.

Figure 1A:
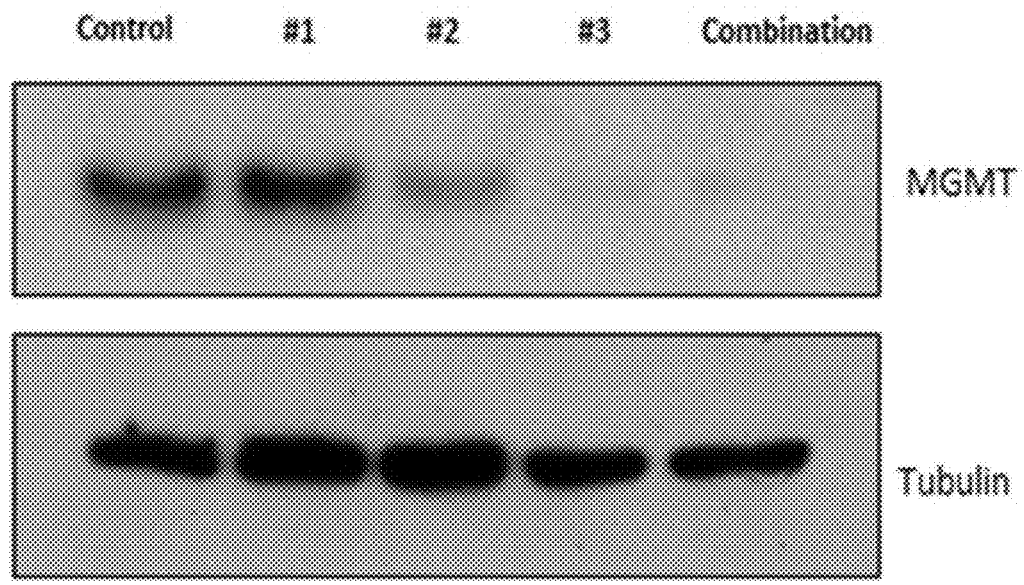
FIG. 1A is an image of a Western Blot showing inhibition of MGMT expression in T98G cell lines by morpholino oligonucleotides comprising SEQ ID NO: 1, SEQ ID NO: 2, and SEQ ID NO: 3 individually, or a combination of SEQ ID NO: 1, SEQ ID NO: 2, and SEQ ID NO: 3 as indicated.

Additional advantages of the invention are set forth in part in the description that follows, and in part will be obvious from the description, or can be learned by practice of the invention. It is to be understood that both the foregoing general description and the following detailed description are exemplary and are not restrictive of the invention as claimed.

SEQUENCE LISTING

SEQ ID NO: 1 is an antisense oligonucleotide that inhibits expression of human MGMT

5'-TTTCGTGCAGACCCTGCTCTT-3'.

SEQ ID NO: 2 is an antisense oligonucleotide that inhibits expression of human MGMT

5'-TTCCATAACACCTGTCTGGTT-3'.

SEQ ID NO: 3 is an antisense oligonucleotide that inhibits expression of human MGMT

5'-ATTCCTTCACGGCCAGTCCTT-3'.

SEQ ID NO: 4 is a control antisense oligonucleotide

5'-CCTCTTACCTCAGTTACAATTTATA-

SEQ ID NO: 5 is a polypeptide sequence of Homo sapiens MGMT.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

Disclosed herein are novel antisense morpholino oligonucleotides (AMONs) and their use in combination with involved field radiation in in-vitro and in-vivo models of solid tumors. Disclosed herein is the surprising result that ionizing radiation can enhance the intracellular delivery of morpholino antisense oligonucleotides to achieve target protein knockdown in in-vitro and in-vivo models.

Definitions

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. For example, in an aspect, a complex comprising a targeting moiety and an oligonucleotide can optionally comprise a detectable label. In an aspect, a disclosed method can optionally comprise repeating the administration of a disclosed composition and/or complex.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In some aspects, preventing malignant cell growth is intended.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or can be treated by a compound or composition that can prevent or inhibit malignant cell growth, prevent or inhibit MGMT protein expression or overexpression in a population of cells, prevent metastasis or tumor growth, reduce tumor size, or a combination thereof. As a further example, "diagnosed with a need for inhibiting MGMT protein expression" refers to having been subjected to a physical examination by a person of skill, for example, a physician, and found to have a condition characterized by malignant cell growth or other disease wherein inducing inhibiting MGMT protein expression of a population of cells would be beneficial to the subject. Such a diagnosis can be in reference to a disorder, such as cancer, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who performed the diagnosis.

As used herein, "homolog" or "homologue" refers to a polypeptide or nucleic acid with homology to a specific known sequence. Specifically disclosed are variants of the nucleic acids and polypeptides herein disclosed which have at least 40, 41, 42, 43, 44, 45, 46, 47, 48, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more percent homology to the stated or known sequence. Those of skill in the art readily understand how to determine the homology of two or more proteins or two or more nucleic acids. For example, the homology can be calculated after aligning the two or more sequences so that the homology is at its highest level. It is understood that one way to define any variants, modifications, or derivatives of the disclosed genes and proteins herein is through defining the variants, modification, and derivatives in terms of homology to specific known sequences.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

Administration: To provide or give a subject an agent, such as a composition comprising therapeutic oligonucleotides by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Antisense: Refers to an oligomeric compound that is at least partially complementary to the region of a target nucleic acid molecule (such as an MGMT transcript) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound. In particular examples, the antisense compound is an antisense oligonucleotide, siRNA or ribozyme.

Binding or stable binding: An association between two substances or molecules, such as the association of an antibody with a peptide, nucleic acid to another nucleic acid, or the association of a protein with another protein or nucleic acid molecule. Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

Biomarker: Molecular, biological or physical attributes that characterize a physiological or cellular state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be any molecular structure produced by a cell or organism. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination.

A biomarker may be represented by the sequence of a nucleic acid from which it can be derived or any other chemical structure. Examples of such nucleic acids include miRNA, tRNA, siRNA, mRNA, cDNA, or genomic DNA sequences including any complimentary sequences thereof.

One example of a biomarker is a gene product, such as a protein or RNA molecule encoded by a particular DNA sequence, such as the MGMT gene. This includes the MGMT protein of SEQ ID NO: 5 disclosed herein.

Cancer: A disease or condition in which abnormal cells divide without control and are able to invade other tissues. Cancer cells spread to other body parts through the blood and lymphatic systems. Cancer is a term for many diseases, there are more than 100 different types of cancer in humans. Most cancers are named after the organ in which they originate. For instance, a cancer that begins in the colon is called a colon cancer. However, the characteristics of a cancer, especially with regard to the sensitivity of the cancer to therapeutic compounds, are not limited to the organ in which the cancer originates.

Cancer is a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

While historically cancers have been and still are characterized by their tissues of origin, more recently, cancers, including solid tumors, have been characterized by other features including expression of gene products such as mRNA or proteins (including cell surface proteins) as well as their resistance or susceptibility to drugs, hormones, or other compounds. Tumors of the type described as being treated herein can be characterized by overexpression of MGMT and/or resistance to temozolamide.

Determining a level of expression of a biomarker: Quantitatively determining expression of a nucleic acid or protein biomarker by routine methods known in the art.

In some examples, an expression level of MGMT is analyzed in a biological sample. Suitable biological samples include samples containing protein obtained from a tumor from a subject, from non-tumor tissue of the subject, from a blood sample from the subject, and/or protein obtained from one or more samples of cancer-free tissue samples or subjects.

MGMT specific antibodies can be used for the detection and quantification of MGMT expression by one of a number of immunoassay methods that are well known in the art, such as those presented in Harlow and Lane (Antibodies, A Laboratory Manual, CSHL, New York, 1988). Methods of constructing such antibodies are known in the art. In addition, such antibodies may be commercially available. Any standard immunoassay format (such as ELISA, Western blot, or RIA assay) can be used to measure MGMT expression.

Effective amount: An amount of agent, such as a morpholino oligonucleotide, that is sufficient to generate a desired response, such as reducing or eliminating a sign or symptom of a condition or disease, such as a cancer characterized by overexpression of MGMT. Such signs or symptoms can include reduction in the rate of growth of a tumor (including halting the growth of a tumor or shrinking a tumor), preventing or otherwise treating metastatic tumor, inhibiting the expression of MGMT protein within a cell, and/or rendering a cell that would otherwise be resistant to temozolamide without the addition of the effective amount of the morpholino oligonucleotide sensitive to temozolamide.

Also, as used herein, the terms "effective amount" and "amount effective" can refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. For example, in some aspects, an effective amount of a disclosed composition is the amount effective to reduce the rate of tumor growth, halt tumor growth and/or inhibit MGMT protein expression in a desired cell or population of cells. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a disclosed composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. In an aspect, a preparation can be administered in a "prophylactically effective amount"; that is, an amount effective for prevention of a disease or condition.

Overexpression or upregulated: As used herein, overexpression of MGMT refers to the expression of sufficient MGMT protein in a tumor cell to render that tumor cell resistant to the effects of temozolamide. Similarly, an effective amount of compounds disclosed herein can inhibit the expression of MGMT sufficiently to cause the same tumor cell to be sensitive to the effects of temozolamide. Methods of measuring MGMT protein are known in the art and include the Western blots described herein. Methods of correlating the expression level of MGMT protein to temozolamide resistance and/or sensitivity are similarly known in the art and described herein.

Polypeptide: Any chain of amino acids, regardless of length or posttranslational modification (such as glycosylation, methylation, ubiquitination, phosphorylation, or the like). In some aspects, a polypeptide is an MGMT polypeptide.

Sample: A sample, such as a biological sample, is a sample obtained from a plant or animal subject. As used herein, biological samples include clinical samples useful for detection of MGMT protein expression and/or resistance of a tumor cell to temozolamide, including, but not limited to, cells, tissues, and bodily fluids, including tissues that are, for example, unfixed, frozen, fixed in formalin and/or embedded in paraffin. In some aspects, the biological sample is obtained from a subject, such as in the form of a set of cells from a solid tumor.

Subject: A living multicellular vertebrate organism, a category that includes, for example, mammals and birds. A "mammal" includes both human and non-human mammals, such as mice. In some aspects, a subject is a patient, such as a patient diagnosed with a tumor characterized by (or suspected to be characterized by) overexpression of MGMT.

Treating a disease: Inhibiting the full development of a disease or condition, for example, in a subject who has a tumor that is characterized by overexpression of MGMT. "Treatment" refers to any therapeutic intervention that ameliorates a sign or symptom of a disease or pathological condition. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits early signs for the purpose of decreasing the risk of developing pathology. A "therapeutic" treatment is a treatment administered after the development of significant signs or symptoms of the disease.

Oligonucleotides

Oligonucleotides are well known to the art. In some aspects, an oligonucleotide can be non-degradable. In some aspects, an oligonucleotide can be water-soluble. In some aspects, an oligonucleotide can be charge-neutral. In some aspects, an oligonucleotide can be water-soluble and charge-neutral. In some aspects, an oligonucleotide can be one or more of the following: non-degradable, water-soluble, and charge-neutral. For example, in some aspects, an oligonucleotide can be non-degradable, water-soluble, and charge-neutral.

In some aspects, an oligonucleotide can be a morpholino.

An oligonucleotide can be chemically synthesized. Synthesis of a single stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 micromolar scale protocol with a 2.5 min coupling step for 2'-O-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the oligonucleotides disclosed herein are known to those of skill in the art.

A single stranded oligonucleotide can comprise a modified nucleotide. Examples of modified nucleotides include, but are not limited to, nucleotides having a 2'-O-methyl (2TOMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in, for example in Sanger, *Principles of Nucleic Acid Structure*, Springer-Verlag Ed. (1984), are also suitable for use in oligonucleotides. Other modified nucleotides include, without limitation: locked nucleic acid (LNA) nucleotides, G-clamp nucleotides, or nucleotide base analogs. LNA nucleotides include but need not be limited to 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc,* 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res,* 29, 2437-2447 (2001)).

An oligonucleotide can comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or nonbridging methylphosphonate or 5'-mercapto moieties (see, e.g., U.S. Pat. No. 5,998,203; Beaucage et al, *Tetrahedron* 49, 1925 (1993)).

Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, peptide nucleic acid, and alkylsilyl substitutions (see, e.g., Hunziker et al, *Modern Synthetic Methods, VCH,* 331-417 (1995); Mesmaeker et al, *Antisense Research, ACS,* 24-39 (1994); Bennett C F and Swayze E E, *Ann Rev Pharmacol Toxicol* 50, 259-293 (2010); incorporated by reference herein). Additional examples of modified nucleotides and types of chemical modifications that can be introduced into the modified oligonucleotides of the present invention are described, e.g., in UK Patent No. GB 2,397,818 B and U.S. Patent Publication Nos. 20040192626 and 20050282188.

An oligonucleotide can comprise one or more non-nucleotides. A non-nucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the oligonucleotide may also comprise attaching a conjugate to the oligonucleotide molecule. The conjugate can be attached at the 5'- and/or the 3'-end of an oligonucleotide via a covalent attachment such as a nucleic acid or non-nucleic acid linker. The conjugate can also be attached to the oligonucleotide through a carbamate group or other linking group (see, e.g., U.S. Patent Publication Nos. 20050074771, 20050043219, and 20050158727). A conjugate may be added to the oligonucleotide for any of a number of purposes. For example, the conjugate may be a molecular entity that facilitates the delivery of the oligonucleotide into a cell or the conjugate a molecule that comprises a drug or label.

Examples of conjugate molecules suitable for attachment to the disclosed oligonucleotides include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; and U.S. Pat. No. 6,753,423, all of which are hereby incorporated by reference for their teaching of conjugate molecules suitable for attachment to oligonucleotides). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325, all of which are hereby incorporated by reference for their teaching of conjugate molecules suitable for attachment to oligonucleotides. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337 which is hereby incorporated by reference for their teaching of conjugate molecules suitable for attachment to oligonucleotides. Additional examples of conjugate molecules include a hydrophobic group, a membrane active compound, a cell penetrating compound, a cell targeting signal, an interaction modifier, or a steric stabilizer as described in U.S. Patent Publication No. 20040167090 which is hereby incorporated by reference for their teaching of conjugate molecules suitable for attachment to oligonucleotides. Further examples include the conjugate molecules described in U.S. Patent Publication No. 20050239739 which is hereby incorporated by reference for their teaching of conjugate molecules suitable for attachment to oligonucleotides.

The type of conjugate used and the extent of conjugation to the oligonucleotide can be evaluated for improved pharmacokinetic profiles, bioavailability, and/or stability of the oligonucleotide while retaining activity. As such, one skilled in the art in light of this disclosure can screen oligonucleotides having various conjugates attached thereto to identify oligonucleotide conjugates having improved properties using any of a variety of well-known in vitro cell culture or in vivo animal models such as those described herein.

Morpholino Oligonucleotides

A morpholino oligonucleotide (MO) is a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides. The morpholino oligonucleotide instead contains a ring nitrogen with coupling through the ring nitrogen (Subbotina E et al, Clin Pharmacol Ther 99, 21-25 (2016); incorporated by reference herein).

Morpholino oligonucleotides can be structures of less than 40, less than 30, less than 25, or 20-23 subunits, including a targeting base sequence that is complementary to a target region of a selected preprocessed mRNA such as an mRNA resulting from the transcription of the MGMT gene. Morpholino oligonucleotides can be composed of morpholino subunits of the form shown in U.S. Pat. Nos. 5,698,685, 5,217,866, 5,142,047, 5,034,506, 5,166,315, 5,521,063, and 5,506,337 (all of which are incorporated in their entirety by reference herein). The synthesis, structures, and binding characteristics of morpholino oligonucleotides are detailed in these patents so that one of skill in the art in light of this disclosure can create the morpholino oligonucleotides with the sequences disclosed herein.

In some aspects, the compositions and methods disclosed herein can utilize a synthetic oligonucleotide analog with a chemically modified backbone. The schematic shown below lists several analogues and compares the properties of these analogues with natural DNA.

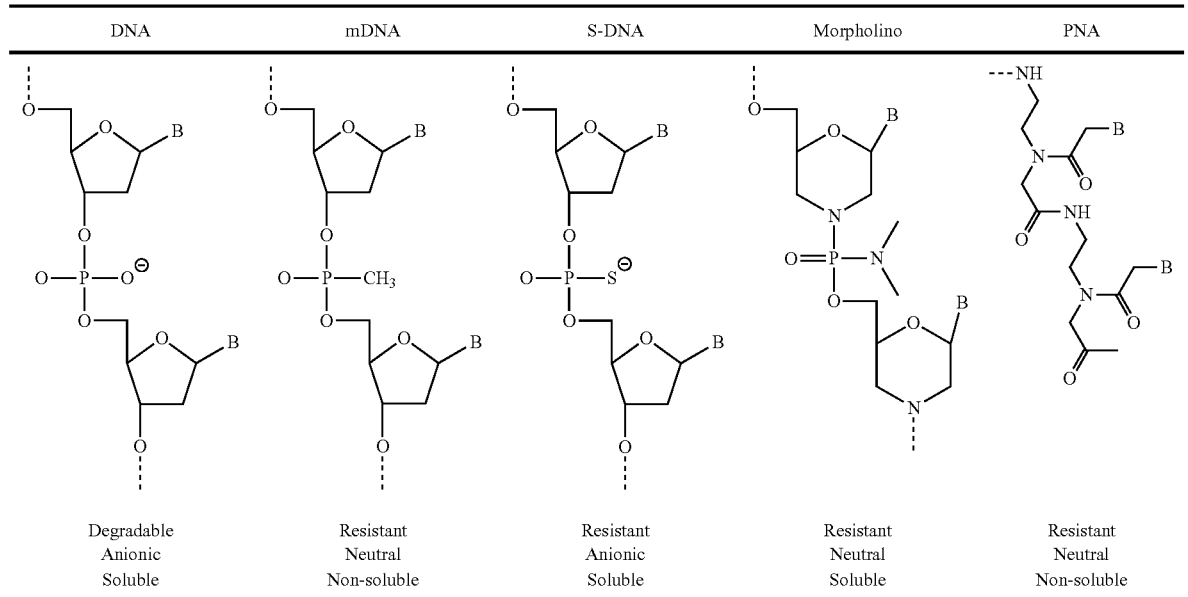

In some aspects, the analogue can be biocompatible and non-degradable, the disclosed compositions and methods can utilize phophorodiamidate morpholino oligonucleotides (also known as morpholinos or MORFs). Morpholinos have a chemically-modified, non-charged backbone and are assembled from four different subunits, each of which contains one of the four nucleobases (A, T, G, and C) linked to a 6-membered morpholine ring. The subunits are joined by non-ionic phosphordiamidate linkages to generate a morpholino oligonucleotide. Morpholinos also possess strong binding affinity (i.e., Kd from the low nM to pM levels), high sequence specificity, and well-demonstrated safety profiles. Furthermore, the immunogenicity of morpholinos is highly sequence dependent, and therefore, can be addressed. The synthesis, structures, and binding characteristics of morpholinos are detailed in U.S. Pat. Nos. 5,698,685, 5,217,866, 5,142,047, 5,034,506, 5,166,315, 5,521,063, and 5,506,337, each of which are incorporated herein by reference in its entirety.

A disclosed morpholino having a longer length provides a higher specificity and a stronger binding affinity; however, such morpholinos also have poorer water-solubility. In the art, a 14 bp-15 bp morpholino is considered the minimal length necessary to maintain ideal targeting effects. A 25 bp morpholino can ensure strong binding affinity and good water-solubility (about 5-30 mM). For example, using 25 bp morpholinos in the disclosed compositions and methods can avoid the impact of steric hindrance on the hybridization of a second morpholino. A longer sequence can provide better "steric flexibility" for hybridization. Accordingly, in the compositions and methods disclosed herein, morpholinos can comprise 10 bp-40 bp. In an aspect, for example, a morpholino can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length.

The A/T/C/G content of a disclosed morpholino can be determined based on three factors: (1) G+C content (# or % of G's and C's), (2) G content (# or % of G's), and (3) C content (# or % of C's).

Regarding G+C content, a disclosed morpholino can comprise a G+C content of about 35% to about 65%. This range can provide optimal binding efficacy and specificity. Regarding G content, a disclosed morpholino can comprise a G content of less than about 36%. This level of G content can provide good aqueous solubility; however, repeats of 4 or more G's should be avoided. Regarding C content, a disclosed morpholinos can comprise a C content of less than 7. This level of C content can ensure that the unfavorable effect of enhancing kidney accumulation of a morpholino can be avoided. In some aspects, conjugation of one or more morpholinos with albumin can favorably alter the pharmacokinetic profiles of the morpholinos and can reduce kidney accumulation (as compared to conjugation of morpholinos and Fab' fragment).

Antisense morpholino oligonucleotides (also termed an aON herein) can be designed to block translation or interfere with RNA processing by steric hindrance and thereby modulate target proteins with specificity (Subbotina 2016 supra and Summerton Biochim Biophys Acta 1489, 141-158 (1999); incorporated by reference herein). Morpholino oligonucleotides are not susceptible to cellular nucleases, do not activate the innate immune response and have limited interactions with cellular proteins due to their uncharged nature. Subbotina 2016 supra and Moulton J D and Jiang S, Molecules 14, 1304-1323 (2009); incorporated by reference herein. Products such as Vivo-Morpholino® have further improved the delivery of morpholino oligonucleotides to a wide array of tissues in animal models.

Antisense morpholino oligonucleotides can interact with membrane bound receptors and can be taken up by absorptive endocytosis or fluid phase pinocytosis (Loke S L et al, Proc Natl Acad Sci USA 86, 3474-3478 (1989); Yakubov L A et al, Proc Natl Acad Sci USA 86, 6454-6458 (1989); Zhao X et al, Expert Opin Drug Deliv 6, 673-686 (2009); and Beltinger C et al, J Clin Invest 95, 1814-1823 (1995); incorporated by reference herein). Ionizing radiation can increase cellular permeability by generating reactive oxygen species (ROS) such as OH—, O2-, H2O2 resulting in oxidative damage to the cell membrane (Maier P et al, Int J Mol Sci 17, doi: 10.3390/ijms17010102 (2016). Ionizing radiation can also enhance intracellular delivery of small particles such as adenoviruses by stimulating endocytosis mediated by dynamin-2, clathrin dependent and non-clathrin dependent pathways that involve $\alpha_v$-integrin, filamentous actin and amiloride sensitive Na+/H+ exchangers (Qian J et al, Cancer Res 65, 5493-5497 (2005); Zhang M et al, Mol Ther 8, 21-28 (2003); and Egami T et al, Clin Cancer Res 14, 1859-1867 (2008); all of which are incorporated by reference herein.

Some antisense compounds do not activate RNase H. RNase-H active oligonucleotides, of which phosphorothioate oligonucleotides are the most prominent example, operate primarily by a mechanism in which the target mRNA is cleaved. RNase-incompetent oligomers, on the other hand, are believed to act by a steric blocking mechanism. Such compounds include morpholino oligonucleotides, PNA's (peptide nucleic acids), methylphosphonates, and 2'-O-alkyl or -allyl modified oligonucleotides, all of which are known in the art.

In a morpholino oligonucleotide, (i) the morpholino groups are linked together by uncharged phosphorus-containing linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444, which is hereby incorporated by reference in its entirety. As shown in the reference, several types of nonionic linkages may be used to construct a morpholino backbone.

Such morpholino oligonucleotides have shown high binding affinity for RNA targets, and the uncharged backbone favors uptake into cells and reduces non-specific binding interactions, relative to charged analogs such as phosphorothioates. They have been shown to provide significantly improved activity and selectivity in inhibiting translation of targeted sequences in comparison to phosphorothioate oligonucleotides. See, for example, Summerton et al., *Antisense & Nucleic Acid Drug Dev.* 7, 63-70, (1997); incorporated by reference herein. The morpholino oligonucleotides have very high nuclease resistance and good water solubility, making them good candidates for in vivo use.

The solubility of the morpholino oligonucleotides, and the ability of the compound to resist precipitation on storage in solution, can be further enhanced by derivatizing the oligomer with a solubilizing moiety, such as a hydrophilic oligomer, or a charged moiety, such as a charged amino acid or organic acid. The moiety may be any biocompatible hydrophilic or charged moiety that can be coupled to the antisense compound and that does not interfere with compound binding to the target sequence. The moiety can be chemically attached to the antisense compound, e.g., at its 5' end, by well-known derivatization methods. One preferred moiety is a defined length oligo ethylene glycol moiety, such as triethyleneglycol, coupled covalently to the 5' end of the antisense compound through a carbonate linkage, via a piperazine linking group forming a carbamate linkage with triethyleneglycol, where the second piperazine nitrogen is coupled to the 5'-end phosphorodiamidate linkage of the antisense. Alternatively, or in addition, the compound may be designed to include one a small number of charged backbone linkages, such as a phosphodiester linkage.

The compound is designed to hybridize to the target sequence under physiological conditions with a $T_m$ substantially greater than 37° C., e.g., at least 50° C. and preferably 60° C.-80° C. Although the compound may not be necessarily 100% complementary to the target sequence, so long as it is effective to stably and specifically bind to the target sequence such that formation of a poly(A) at intron 9 is inhibited. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target and inhibition of MGMT protein expression.

Because morpholino oligonucleotides have bases that are analogs of those of nucleic acids, a description of a morpholino oligonucleotide as having a particular sequence (or a homolog thereof) is a recitation of the structure of the morpholino oligonucleotide.

Chemical modification of the morpholino oligonucleotide with one or more conjugates can be performed as described above.

In some aspects, any of the morpholino oligonucleotide sequences described herein can be a variant.

As you used herein, the term "nucleic acid sequence" or "nucleic acid molecule" or polynucleotide are used interchangeably and refer to a DNA or RNA molecule in single or double stranded form. An "isolated nucleic acid sequence" refers to a nucleic acid sequence which is no longer in the natural environment from which it was isolated, e.g., the nucleic acid sequence in a cell.

A "mutation" in a nucleic acid molecule is a change of one or more nucleotides compared to the wild type sequence, e.g. by replacement, deletion or insertion of one or more nucleotides. A "point mutation" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned. For example, sequence similarity or identity can be determined by searching against databases such as FASTA, BLAST, etc., but hits should be retrieved and aligned pairwise to compare sequence identity. Two proteins or two protein domains, or two nucleic acid sequences can have "substantial sequence identity" if the percentage sequence identity is at least 70%, 75%, 80%, 85%, 90%, 95%, 98%, 99% or more, preferably 90%, 95%, 98%, 99% or more. Such sequences are also referred to as "variants" herein, e.g., other variants of antisense oligomeric compounds. It should be understood that sequence with substantial sequence identity do not necessarily have the same length and may differ in length. For example sequences that have the same nucleotide sequence but of which one has additional nucleotides on the 3'- and/or 5'-side are 100% identical.

A "variant" refers to a molecule substantially similar to the antisense oligomeric compound, morpholino or a fragment thereof, such as a nucleotide substitution variant having one or more substituted nucleotides, but which maintains the ability to hybridize with the particular gene. Preferably the variant comprises the mutations as identified by the invention. Variants also include longer sequences.

Disclosed herein are morpholino oligonucleotides. In some aspects, the morpholino oligonucleotides can comprise a sequence selected from SEQ ID NO: 1, SEQ ID NO: 2, or SEQ ID NO: 3. In some aspects, the morpholino oligonucleotides can be no more than 40 subunits in length. In some aspects, the morpholino oligonucleotides can be no more than 25 subunits in length. In some aspects, the morpholino oligonucleotide can consist of a sequence selected from SEQ ID NO: 1, SEQ ID NO: 2, or SEQ ID NO: 3.

Pharmaceutical Compositions

A pharmaceutical composition can be any chemical compound or composition capable of inducing a desired therapeutic effect when an effective amount is properly administered to a subject. A pharmaceutical composition can include a therapeutic agent, a diagnostic agent or a pharmaceutical agent. A therapeutic agent is one that alone or together with one or more additional compounds induces the desired response (such as inducing a therapeutic effect when administered to a subject). In some aspects, a pharmaceutical agent is an agent that significantly reduces one or more symptoms associated with cancer, particularly a cancer comprising a tumor that is characterized by MGMT overexpression. One example of such a pharmaceutical composition is one that comprises one or more of the disclosed morpholino oligonucleotides alone or in combination that is sufficient to inhibit MGMT protein expression in a tumor.

A pharmaceutically acceptable carrier (interchangeably termed a vehicle) can be any material or molecular entity that facilitates the administration or other delivery of the morpholino oligonucleotides described herein. In general, the type of carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some aspects, the carrier is one that allows trafficking of the morpholino oligonucleotide to the tumor or allows the morpholino oligonucleotide to be taken up by the tumor, or even more particularly allows selective trafficking or uptake of the morpholino oligonucleotide to the tumor.

An effective amount or concentration of a compound may be any amount of a composition that alone, or together with one or more additional therapeutic agents is sufficient to achieve a desired effect in a subject, or in a cell being treated with the agent. The effective amount of the agent will be dependent on several factors, including, but not limited to, the subject or cells being treated and the manner of administration of the therapeutic composition. In some aspects, an effective amount or concentration is one that is sufficient to prevent advancement, delay progression, or to cause regression of a disease, or which is capable of reducing symptoms caused by any disease, including cancer, including cancer comprising a tumor characterized by overexpression of MGMT.

The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to the sign or symptom in the absence of the composition. A therapeutically effective amount of a pharmaceutical composition can be administered in a single dose, or in several doses, for example daily, during a course of treatment. However, the therapeutically effective amount can depend on the subject being treated, the severity and type of the condition being treated, and the manner of administration. For example, an effective amount of such agent can vary from about 100 µg-10 mg per kg body weight if administered intravenously.

The actual dosages will vary according to factors such as the particular status of the subject (for example, the subject's age, size, fitness, extent of symptoms, susceptibility factors, and the like) time and route of administration, other drugs or treatments being administered concurrently, as well as the specific pharmacology of treatments for cancer eliciting the desired activity or biological response in the subject. Dosage regimens can be adjusted to provide an optimum prophylactic or therapeutic response.

An effective amount is also one in which any toxic or detrimental side effect(s) of the compound and/or other biologically active agent is outweighed in clinical terms by therapeutically beneficial effects. A non-limiting range for a therapeutically effective amount of treatments for cancer characterized by MGMT overexpression within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight to about 10 mg/kg body weight per dose.

The effective amount can be selected based on the mode of delivery, for example, trans-epidermal, rectal, oral, pulmonary, intranasal delivery, intravenous or subcutaneous delivery.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models. Using such models, ordinary calculations and adjustments can be done to determine an appropriate concentration and dose to administer a therapeutically effective amount of the compound.

Disclosed herein are pharmaceutical compositions comprising any of the morpholino oligonucleotides disclosed herein alone or in combination with any of the morpholino oligonucleotides disclosed herein. In some aspects, the pharmaceutical compositions can further comprise a pharmaceutically acceptable carrier. In some aspects, the morpholino oligonucleotides can comprise a sequence selected from SEQ ID NO: 1, SEQ ID NO: 2, or SEQ ID NO: 3. In some aspects, the morpholino oligonucleotide can be no more than 40 subunits in length. In some aspects, the morpholino oligonucleotide can be no more than 25 subunits in length. In some aspects, the morpholino oligonucleotide can consist of a sequence selected from SEQ ID NO: 1, SEQ ID NO: 2, or SEQ ID NO: 3.

Disclosed herein are pharmaceutical compositions, wherein the morpholino oligonucleotide can comprise SEQ ID NO: 1 and not SEQ ID NO: 2 and SEQ ID NO: 3. Disclosed herein are pharmaceutical compositions, wherein the morpholino oligonucleotide can comprise SEQ ID NO: 2 and not SEQ ID NO: 1 and SEQ ID NO: 3. Disclosed herein are pharmaceutical compositions, wherein the morpholino oligonucleotide can comprise SEQ ID NO: 3 and not SEQ ID NO: 1 and SEQ ID NO: 2. Disclosed herein are pharmaceutical compositions, wherein the morpholino oligonucleotide can comprise SEQ ID NO: 1 and SEQ ID NO: 2 and not SEQ ID NO: 3. Disclosed herein are pharmaceutical compositions, wherein the morpholino oligonucleotide can comprise SEQ ID NO: 1 and SEQ ID NO: 3 and not SEQ ID NO: 2. Disclosed herein are pharmaceutical compositions, wherein the morpholino oligonucleotide can comprise SEQ ID NO: 2 and SEQ ID NO: 3 and not SEQ ID NO: 1. In some aspects, the morpholino oligonucleotide can comprise SEQ ID NO: 1, SEQ ID NO: 2, and SEQ ID NO: 3.

In some aspects, any of the pharmaceutical compositions disclosed herein can be formulated for intravenous administration.

In some aspects, any of the pharmaceutical compositions disclosed herein can be administered to a subject in need of treatment of a cancer. For example, in some aspects, any of pharmaceutical compositions disclosed herein can be administered to a subject in need of treating a tumor. In some aspects, the tumor can overexpress MGMT.

The pharmaceutical carrier employed can be, for example, a solid, liquid, or gas. Examples of solid carriers include but are not limited to lactose, terra alba, sucrose, talc, gelatin, agar, pectin, acacia, magnesium stearate, and stearic acid. Examples of liquid carriers include but are not limited to sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Tablets and capsules are the preferred oral dosage units whereby solid pharmaceutical carriers are employed. Optionally, tablets can be coated by standard aqueous or nonaqueous techniques. A tablet containing a composition or complex disclosed herein can be prepared by compression or molding, optionally with one or more accessory ingredients or adjuvants. Compressed tablets can be prepared by compressing, in a suitable machine, a disclosed complex of composition in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

It is understood that the disclosed compositions can be prepared from the disclosed compounds. It is also understood that the disclosed compositions can be employed in the disclosed methods of using.

Methods of Treatment

Disclosed herein are methods of treating a subject that has cancer. In some aspects, the cancer can be a solid tumor. In some aspects, the solid tumor can be characterized by MGMT overexpression. The methods of treatment can comprise administering one or more of the morpholinos or pharmaceutical compositions described herein. In some aspects, the cancer can be a primary or secondary tumor. In some aspects, the cancer can be a metastatic tumor. In some aspects, the primary or secondary tumor is within the patient's lung or brain. In some aspects, the cancer has metastasized. In some aspects, the cancer may originate in the lung or brain and metastasize to one or more sites.

Disclosed herein, are methods of treating a patient with cancer. The cancer can be any cancer. In some aspects, the cancer can be lung cancer, non-small cell lung cancer, brain cancer or a glioma. In some aspects, the subject has been diagnosed with cancer prior to the administering step.

In some aspects, the methods can comprise treating a tumor in a subject. In some aspects, the methods of treating a tumor in a subject can include administering systemically any of the morpholinos or pharmaceutical compositions disclosed herein to the subject. In some aspects, the tumor overexpresses MGMT or can be characterized by overexpression of MGMT.

In some aspects, the methods can further comprise administering one or more doses of ionizing radiation to the tumor. In some aspects, the dose of radiation can be at least 1 Gy. In some aspects, the methods of claim 10, the dose of radiation can be at least 5 Gy.

In some aspects, the dose of ionizing radiation can be administered to the tumor prior to the administration of any of the pharmaceutical compositions disclosed herein to the subject. In some aspects, the dose of radiation can be administered at least 24 hours prior to administration of the pharmaceutical composition.

In some aspects, in any of the methods disclosed herein, temozoloamide can be administered to the subject. In some aspects, the administration of temozoloamide can be administered prior to, simultaneously, or after the administration of the dose of ionizing radiation. In some aspects, the administration of temozoloamide can be administered prior to, simultaneously, or after the administration of any of the pharmaceutical compositions disclosed herein. In some aspects, the pharmaceutical composition can be administered intravenously.

In any of the methods disclosed herein, the method can further include a step of determining whether the tumor overexpresses MGMT. In some aspects, the method can include the step of determining that the tumor overexpresses MGMT. In some aspects, the step of determining that the tumor overexpresses MGMT can comprise measuring expression of MGMT protein or measuring resistance to temozolomide in a sample of cells obtained from the tumor.

Also disclosed herein are methods of enhancing delivery of one or more morpholino oligonucleotides. In some aspects, the methods can comprise administering to a subject with cancer a therapeutically effective amount dose of radiation prior to administering a therapeutically effective amount of the one or more morpholino oligonucleotides described herein. In some aspects, the one or more morpholino oligonucleotides can comprise a sequence selected from SEQ ID NO: 1, SEQ ID NO: 2, or SEQ ID NO: 3. In some aspects, the morpholino oligonucleotide can be no more than 40 subunits in length. In some aspects, the one or more morpholino oligonucleotides can consist of a sequence selected from SEQ ID NO: 1, SEQ ID NO: 2, or SEQ ID NO: 3. In some aspects, the morpholino oligonucleotide can comprise SEQ ID NO: 1 and not SEQ ID NO: 2 and SEQ ID NO: 3; SEQ ID NO: 2 and not SEQ ID NO: 1 and SEQ ID NO: 3; SEQ ID NO: 3 and not SEQ ID NO: 1 and SEQ ID NO: 2; SEQ ID NO: 1 and SEQ ID NO: 2 and not SEQ ID NO: 3; SEQ ID NO: 1 and SEQ ID NO: 3 and not SEQ ID NO: 2; or SEQ ID NO: 2 and SEQ ID NO: 3 and not SEQ ID NO: 1. In some aspects, the dose of radiation can be administered at least 24 hours prior to the administration of the one or more morpholino oligonucleotides.

Further disclosed herein are methods of enhancing the efficacy of temozolamide. In some aspects, the methods can comprise administering a therapeutically effect amount of one or more morpholino oligonucleotides described herein prior to administering a therapeutically effective amount of temozolamide. In some aspects, the one or more morpholino oligonucleotides can comprise a sequence selected from SEQ ID NO: 1, SEQ ID NO: 2, or SEQ ID NO: 3. In some aspects, the morpholino oligonucleotide can be no more than 40 subunits in length. In some aspects, the one or more morpholino oligonucleotides can consist of a sequence selected from SEQ ID NO: 1, SEQ ID NO: 2, or SEQ ID NO: 3. In some aspects, the morpholino oligonucleotide can comprise SEQ ID NO: 1 and not SEQ ID NO: 2 and SEQ ID NO: 3; SEQ ID NO: 2 and not SEQ ID NO: 1 and SEQ ID NO: 3; SEQ ID NO: 3 and not SEQ ID NO: 1 and SEQ ID NO: 2; SEQ ID NO: 1 and SEQ ID NO: 2 and not SEQ ID NO: 3; SEQ ID NO: 1 and SEQ ID NO: 3 and not SEQ ID NO: 2; or SEQ ID NO: 2 and SEQ ID NO: 3 and not SEQ ID NO: 1. In some aspects, the one or more morpholino oligonucleotides can be administered at least 24 hours prior to the administration of the temozolamide.

Also disclosed herein are methods of inducing apoptosis. In some aspects, the methods can comprise contacting a population of cells with a composition comprising a morpholino oligonucleotide sequence selected from SEQ ID NO: 1, SEQ ID NO: 2, or SEQ ID NO: 3, wherein the contacting of the cells with the composition induces apoptosis of the cells. In some aspects, the the morpholino oligonucleotide can be no more than 40 subunits in length. In some aspects, the morpholino oligonucleotides can consist of a sequence selected from SEQ ID NO: 1, SEQ ID NO: 2, or SEQ ID NO: 3. In some aspects, the morpholino oligonucleotide can comprise SEQ ID NO: 1 and not SEQ ID NO: 2 and SEQ ID NO: 3; SEQ ID NO: 2 and not SEQ ID NO: 1 and SEQ ID NO: 3; SEQ ID NO: 3 and not SEQ ID NO: 1 and SEQ ID NO: 2; SEQ ID NO: 1 and SEQ ID NO: 2 and not SEQ ID NO: 3; SEQ ID NO: 1 and SEQ ID NO: 3 and not SEQ ID NO: 2; or SEQ ID NO: 2 and SEQ ID NO: 3 and not SEQ ID NO: 1. In some aspects, the methods can further comprise administering temozolamide. In some aspects, the composition comprising the morpholino oligonucleotide can be administered at least 24 hours prior to the administration of the temozolamide. In some aspects, the methods can further comprise repeating the contacting of the cells with the composition. In some aspects, the cells can overexpress MGMT. In some aspects, the cells can be malignant cells. In some aspects, the malignant cells can be lung cells or brain cells. In some aspects, the cells can be in a subject. In some aspects, the subject can have a glioma or non-small cell lung cancer.

The administration of pharmaceutical compositions can be for either prophylactic or therapeutic purposes. When provided prophylactically, the pharmaceutical composition is provided in advance of any clinical symptom. When provided therapeutically, the compounds are provided in response to symptoms of the disease. For prophylactic and therapeutic purposes, the pharmaceutical compositions described herein can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol) or as repeated doses within a prolonged prophylaxis or treatment regimen that will yield clinically significant results to alleviate one or more symptoms or detectable conditions associated with the disease.

A subject can be any multi-cellular vertebrate organism, a category that includes human and non-human mammals, such as mice. In some aspects, the subject can be a human. In some aspects, the subject can be a human patient. In some aspects, a subject can be a male. In some aspects, a subject can be a female. Further types of subjects to which the pharmaceutical composition may be properly administered include subjects known to have cancer, including cancers with tumors characterized by overexpression of MGMT.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient.

A patient refers to a subject afflicted with one or more diseases or disorders, such as, for example, a cancer. In some aspects, the cancer, the tumor, one or more cancerous cells can overexpress MGMT.

In some aspects, a patient has been diagnosed with a need for treatment of cancer prior to the administering step. In some aspects, a patient has been diagnosed with a need for inhibiting MGMT protein expression in one or more malignant cells, or tumor; reducing one or more symptoms of a cancer; reducing rate of growth of cancer; reducing the size of a tumor; or a combination thereof.

Administration of the pharmaceutical composition can be by any method of providing or giving a subject a pharmaceutical composition, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Treating a subject encompasses any therapeutic intervention that can ameliorate a sign or symptom of a disease or pathological condition after it has begun to develop, whether or not the subject has developed symptoms of the disease. Ameliorating, with reference to a disease, pathological condition or symptom refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the memory and/or cognitive function of the subject, a qualitative improvement in symptoms observed by a clinician or reported by a patient, or by other parameters well known in the art that are specific to cancers.

A symptom may be any subjective evidence of disease or of a subject's condition, for example, such evidence as perceived by the subject; a noticeable change in a subject's condition indicative of some bodily or mental state. A sign may be any abnormality indicative of disease, discoverable on examination or assessment of a subject. A sign is generally an objective indication of disease.

Treating a subject with cancer with any of pharmaceutical compositions disclosed herein can be performed in combination with other therapeutic moieties including radiotherapy and chemotherapy. The treatment can be performed in any combination. In some aspects, a dose of ionizing radiation can be administered prior to the administration of any of the pharmaceutical compositions disclosed herein. The dose of ionizing radiation can be given 1 hour, 3 hours, 8 hours, 12 hours, 16 hours, 24 hours, 36 hours, 48 hours, 72 hours or more in advance of the administration of any of the pharmaceutical compositions disclosed herein. The ionizing radiation can be targeted to the tumor thereby sparing the rest of the body.

In some aspects, the disclosed pharmaceutical composition can be administered in combination with a known chemotherapeutic agent such as temozolamide. Dosing with temozolamide (and other pharmaceutical compositions) is known in the art and can be altered to be used in combination with the disclosed pharmaceutical compositions by one of skill in the art in light of this disclosure. The temozolamide can be given concurrently with, prior to or after the administration of any of the disclosed pharmaceutical compositions.

In some aspects, the disclosed pharmaceutical composition can be administered in combination with both ionizing radiation and a known chemotherapeutic agent such as temozolamide. In some aspects, the ionizing radiation can be administered prior to the disclosed pharmaceutical composition as well as the known chemotherapeutic agent which can in turn be administered at any time relative to one another.

Kits

Disclosed herein are kits comprising one or more morpholino oligonucleotides or pharmaceutical compositions disclosed herein. In some aspects, a disclosed kit can comprise instructions for administering one or more of the morpholino oligonucleotides or pharmaceutical compositions disclosed herein. In some aspects, the one or more morpholino oligonucleotides comprise SEQ ID NO: 1, SEQ ID NO: 2, SEQ ID NO: 3, or a combination thereof.

Disclosed herein are kits comprising a morpholino oligonucleotide comprising the sequence of SEQ ID NO: 1 and not SEQ ID NO: 2 and SEQ ID NO: 3. Disclosed herein are kits comprising a morpholino oligonucleotide comprising the sequence of SEQ ID NO: 2 and not SEQ ID NO: 1 and SEQ ID NO: 3. Disclosed herein are kits comprising a morpholino oligonucleotide comprising the sequence of SEQ ID NO: 3 and not SEQ ID NO: 1 and SEQ ID NO: 2. Disclosed herein are kits comprising a morpholino oligonucleotide comprising the sequence of SEQ ID NO: 1 and SEQ ID NO: 2 and not SEQ ID NO: 3. Disclosed herein are kits comprising a morpholino oligonucleotide comprising the sequence of SEQ ID NO: 1 and SEQ ID NO: 3 and not SEQ ID NO: 2. Disclosed herein are kits comprising a morpholino oligonucleotide comprising the sequence of SEQ ID NO: 2 and SEQ ID NO: 3 and not SEQ ID NO: 1. Disclosed herein are kits comprising a morpholino oligonucleotide comprising the sequence of SEQ ID NO: 1, SEQ ID NO: 2, and SEQ ID NO: 3.

In some aspects, any combination of morpholino oligonucleotides comprising the sequence of SEQ ID NO: 1, SEQ ID NO: 2, and/or SEQ ID NO: 3 can be co-formulated. In some aspects, any combination of morpholino oligonucleotides comprising the sequence of SEQ ID NO: 1, SEQ ID NO: 2, and/or SEQ ID NO: 3 can be co-packaged.

Disclosed herein are kits further comprising temozoloamide. Disclosed herein are kits further comprising one or more doses of ionizing radiation.

The compositions described herein can be packaged in a suitable container labeled, for example, for use as a therapy to treat cancer or any of the methods disclosed herein. Accordingly, packaged products (e.g., sterile containers containing the composition described herein and packaged for storage, shipment, or sale at concentrated or ready-to-use concentrations) and kits, including at least one or more morpholino oligonucleotides as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent. Alternatively, the compounds can be provided in a concentrated form with a diluent and instructions for dilution.

In an aspect, morpholino oligonucleotides comprising the sequence of SEQ NO: 1, SEQ ID NO: 2 and SEQ ID NO: 3 can be co-packaged. In an aspect, morpholino oligonucleotides comprising the sequence of SEQ NO: 1 and SEQ ID NO: 2 can be co-packaged. In an aspect, morpholino oligonucleotides comprising the sequence of SEQ NO: 1 and SEQ ID NO: 3 can be co-packaged. In an aspect, morpholino oligonucleotides comprising the sequence of SEQ NO: 2 and SEQ ID NO: 3 can be co-packaged.

EXAMPLES

The following examples are for illustration only. In light of this disclosure, those of skill in the art will recognize that variations of these examples and other examples of the disclosed invention be possible without undue experimentation.

Example 1—Specific AMONs Suppress MGMT Enzyme Expression in Tumor Cell Lines The ability of each of three AMONs (SEQ ID NO: 1, SEQ ID NO: 2, and SEQ ID NO: 3) to inhibit MGMT expression in tumor cell lines was assessed. Three MGMT expressing solid tumor cell lines (T98G Glioma, H460 and A549 non-small-cell-lung cancer cell lines) were transduced with AMONs using a scrape-loading technique (Partridge M et al, Antisense Nucleic Acid Drug Dev 6, 169-175 (1996); incorporated by reference herein). A Western blot assay (FIG. 1A) shows that AMONs of SEQ ID NO: 2 alone, SEQ ID NO: 3 alone, or the combination of SEQ ID NO: 1, SEQ ID NO: 2 and SEQ ID NO: 3 were most effective in silencing MGMT expression. This was replicated in H460 and A549 NSCLC lines.

Figure 1B:
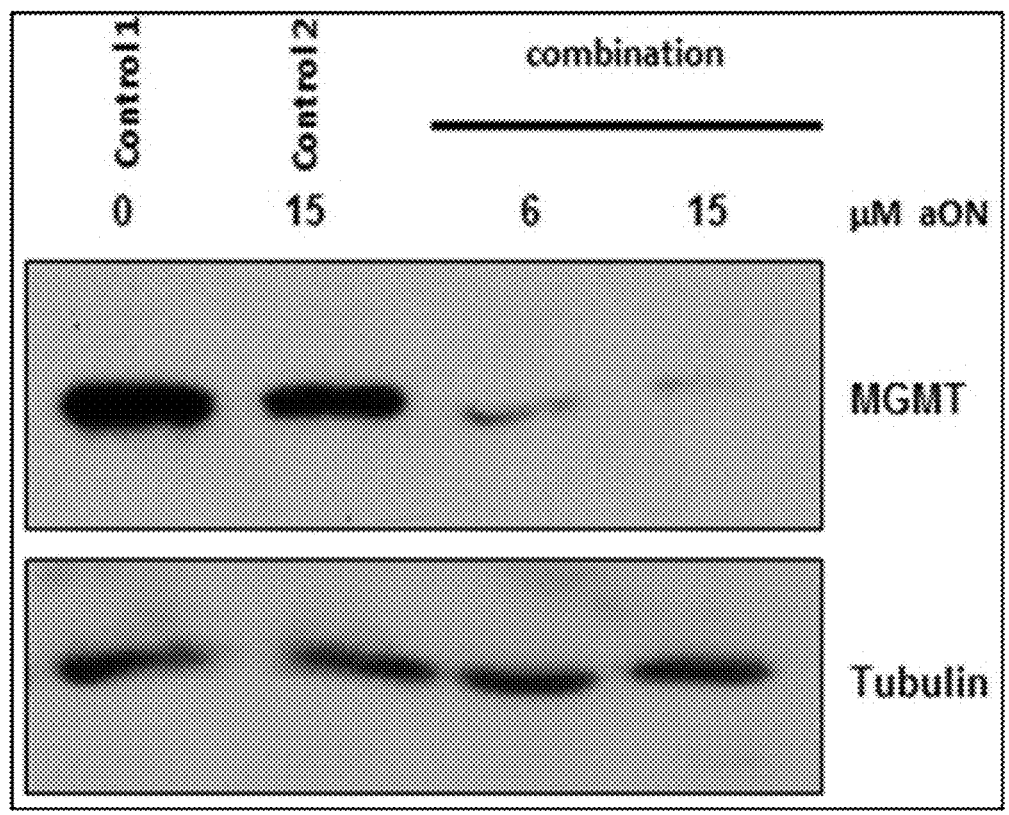
FIG. 1B is an image of a Western blot showing inhibition of MGMT expression in H460 NSCLC cell lines in the presence of a 1:1:1 combination of morpholino oligonucleotides of SEQ ID NO: 1, SEQ ID NO: 2, and SEQ ID NO: 3 at 6 μM and 15 μM as indicated. The control2 includes a negative control morpholino oligonucleotide of SEQ ID NO: 4.
Figure 1C:
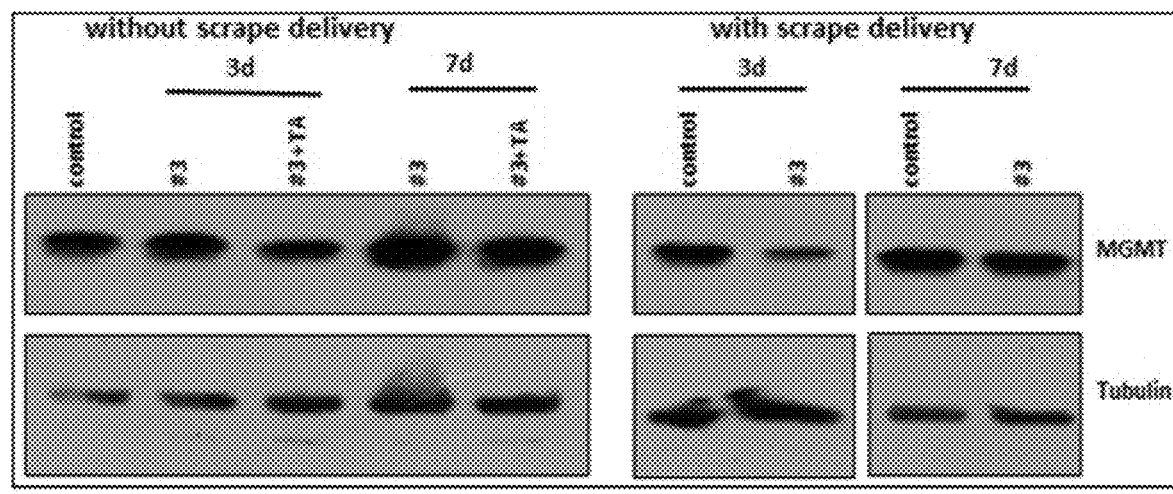
FIG. 1C is an image of a Western blot showing inhibition of MGMT in T98G cells by an oligonucleotide of SEQ ID NO: 3 delivered by either scrape delivery or a lipofectamine transfection reagent as indicated. Cellular lysates were collected 3 and 7 days after treatment with the morpholino oligonucleotide as indicated.

Lysosomal transfection agents were also used to introduce the AMONs into the cells and produced similar results (FIG. 1B). MGMT silencing was not achieved when cells were exposed to AMONS without scrape-loading or liposomal transfection agents (controls). Inhibition of MGMT expression using the oligonucleotide of SEQ ID NO: 3 was transient in T98G cell lines with the best inhibition of MGMT expression observed at 3 days with restoration of MGMT expression by 7 days with both scrape-loading and liposomal transfection agents (FIG. 1C).

Figure 2A:
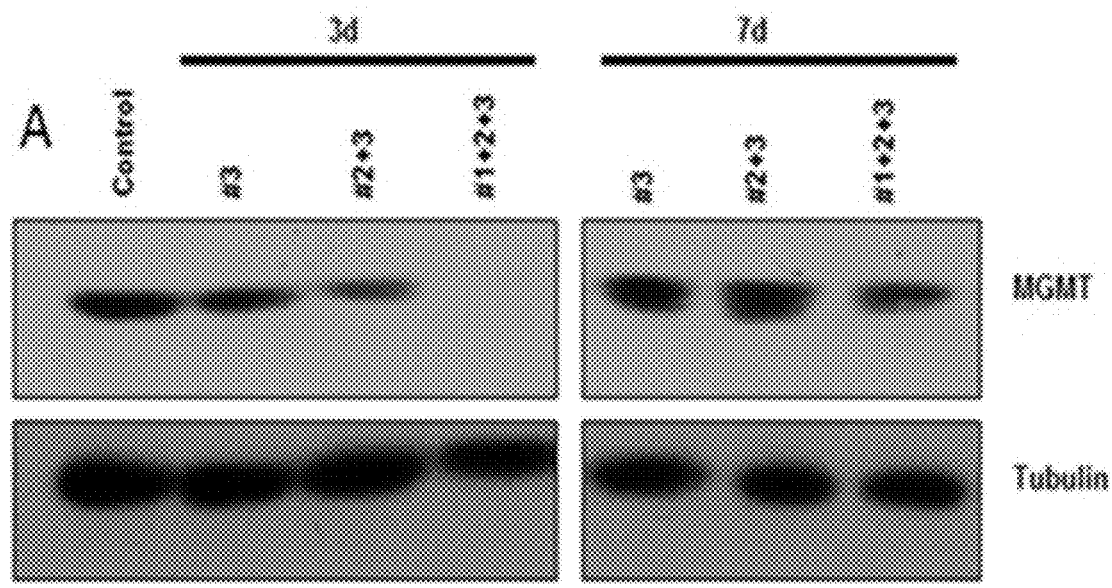
FIG. 2A is an image of a Western blot showing inhibition of MGMT in T98G cells by combinations of morpholino oligonucleotides—those combinations shown are SEQ ID NO: 3 (and no other specific oligonucleotides), SEQ ID NO: 2 and SEQ ID NO: 3, and SEQ ID NO: 1, SEQ ID NO: 2, and SEQ ID NO: 3. Cellular lysates were collected 3 and 7 days after treatment with the morpholino oligonucleotide combination as indicated.

Example 2—Ionizing Radiation can Enhance AMON Delivery and Effectively Suppress MGMT without the Use of Scrape-Loading or Liposomal Transfection Agents The ability of ionizing radiation to enhance the cytosolic delivery of AMONs in T98G glioma cell lines and suppress MGMT expression was assessed. T98 G cells were exposed to AMON SEQ ID NO: 2 alone, SEQ ID NO: 3 alone, or the combination of SEQ ID NO: 1, SEQ ID NO: 2 and SEQ ID NO: 3, one hour after exposure to 1 Gy of ionizing radiation. A Western blot assay shows that the combination of sequences 1, 2 and 3, three days after exposure to AMONs (FIG. 2A) was most effective at inhibiting MGMT expression. As with the use of scrape loading and lysosomal transfection agents, the inhibition of expression with radiation enhanced delivery of AMONS was transient, with peak inhibition at 3 days and restoration of MGMT expression by 7 days. Based on these findings a combination of sequences 1, 2 and 3 were used for further experiments.

Figure 2B:
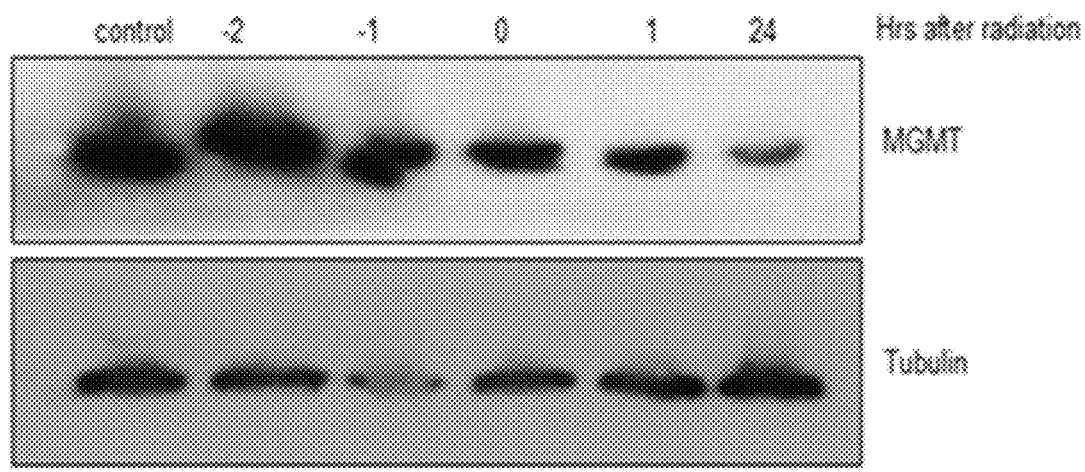
FIG. 2B is an image of a Western blot showing inhibition of MGMT in T98G cells by a combination of morpholino oligonucleotides of SEQ ID NO: 1, SEQ ID NO: 2, and SEQ ID NO: 3. Cells were treated with the morpholino oligonucleotides before or after exposure to 1 Gy radiation as indicated.
Figure 2C:
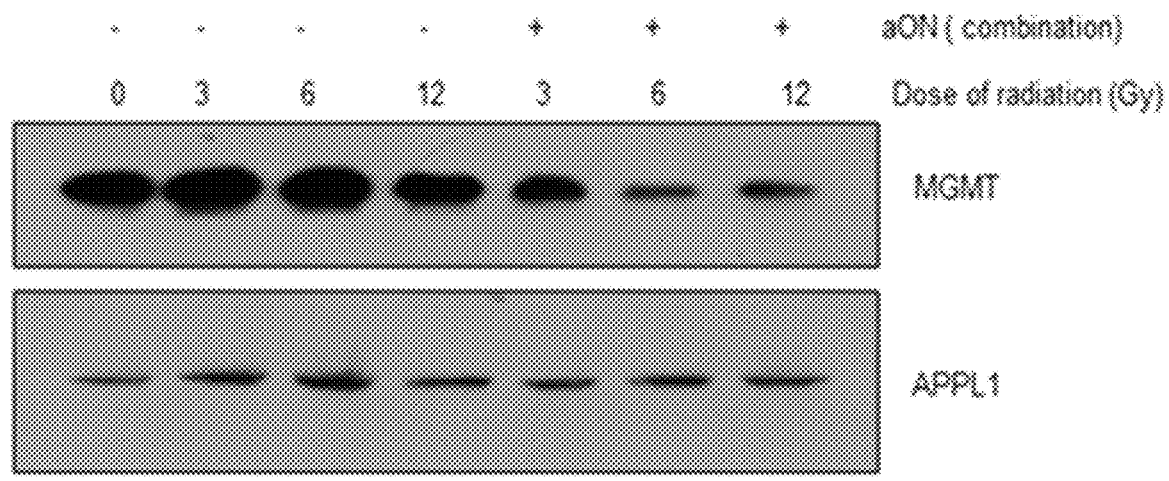
FIG. 2C is an image of a Western blot showing inhibition of MGMT in T98G cells by a combination of morpholino oligonucleotides of SEQ ID NO: 1, SEQ ID NO: 2, and SEQ ID NO: 3 24 hours after exposure to the dose of radiation indicated.

To determine the optimal timing for exposure to AMON with respect to exposure to radiation, T98G cell lines were exposed to AMONs 2 hours and 1 hour before radiation as well as 1 and 24 hours after radiation exposure (FIG. 2B). The best inhibition was observed when cells were exposed to AMON 24 hours after radiation. This time line was adopted for further experiments. Different tumor cell lines required different doses of radiation to enhance delivery of AMON. Knockdown could be achieved in T98G cell lines at 1 Gy while H460 and A549 cell lines required exposure to 6-12 Gy for best results with no inhibition at lower doses of ionizing radiation (FIG. 2C).

Figure 3:
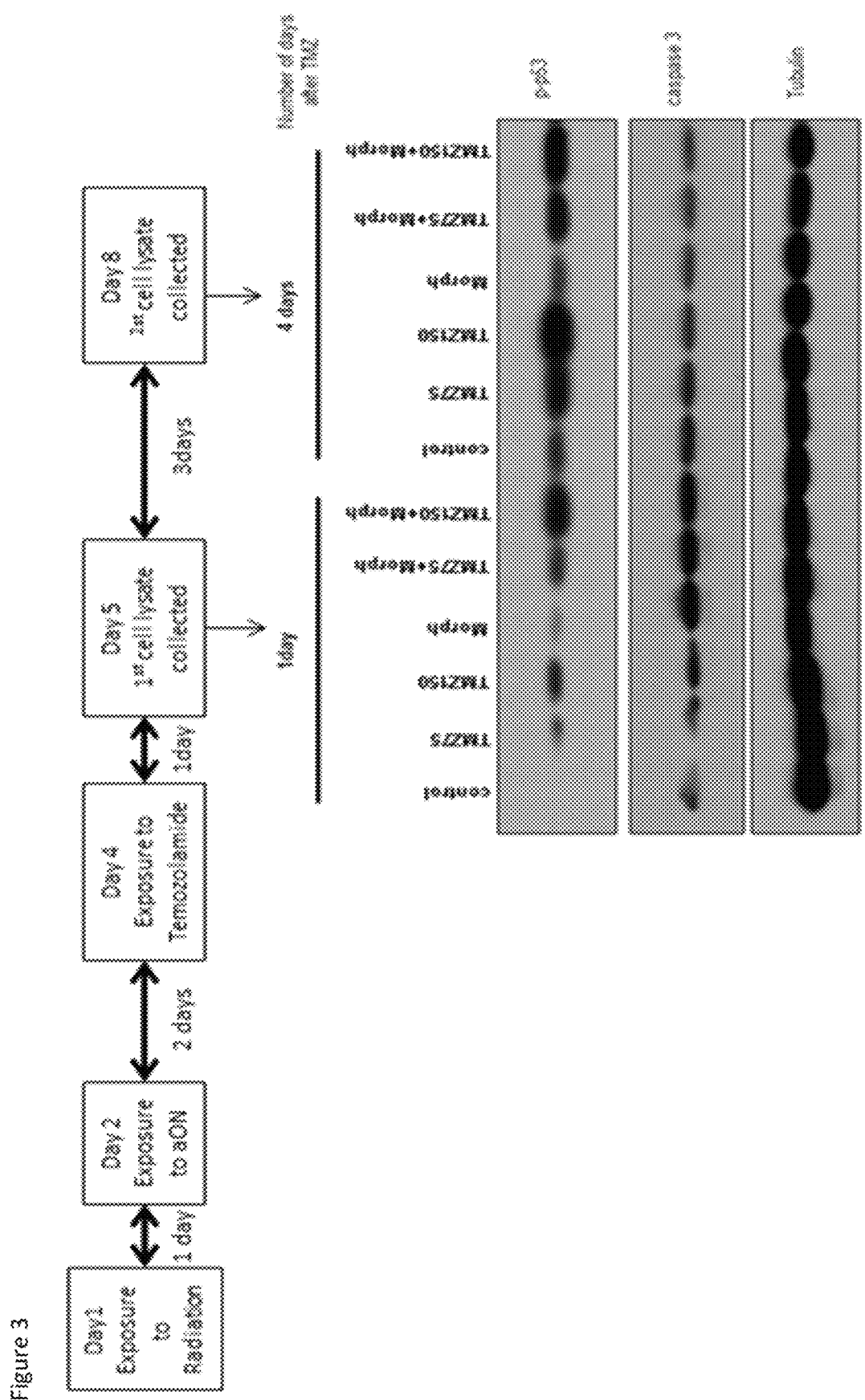
FIG. 3 is a flow chart of an experimental model that includes treatment of cells with radiation, morpholino oligonucleotides of SEQ ID NO: 1, SEQ ID NO: 2, and SEQ ID NO: 3, and 75 or 150 μg/ml temozolamide as indicated. The Figure also includes an image of a Western blot showing expression of phosphorylated-p53 and caspase 3 indicating enhanced cytotoxic effects of temozolamide in combination with the morpholino oligonucleotides and radiation.

Example 3—Radiation Enhanced Delivery of AMONs Enhances the Cytotoxic Effects of Temozolamide MGMT expressing glioma cell lines such as T98G are known to be resistant to the cytotoxic effects of temozolomide (Yoshino A et al, Int J Oncol 36, 1367-1377 (2010); incorporated by reference herein). AMONs were administered 1 day after exposure of the T98G cells to 1 Gy of radiation and 75 or 150 µg/ml temozolamide administered two days after administration of the AMONs. Whole cell lysates were then collected 1 and 4 days after exposure to the temozolamide and a Western blot using antibodies specific for the indicated proteins performed. The results shown in FIG. 3 indicate that the delivery of AMONs renders T98G cell lines susceptible to temozolomide. The enhanced cytotoxic effects of temozolamide appeared to be dose dependent with greater apoptosis after exposure to 150 μg/mL relative to 75 μg/mL of temozolomide.

Figure 4A:
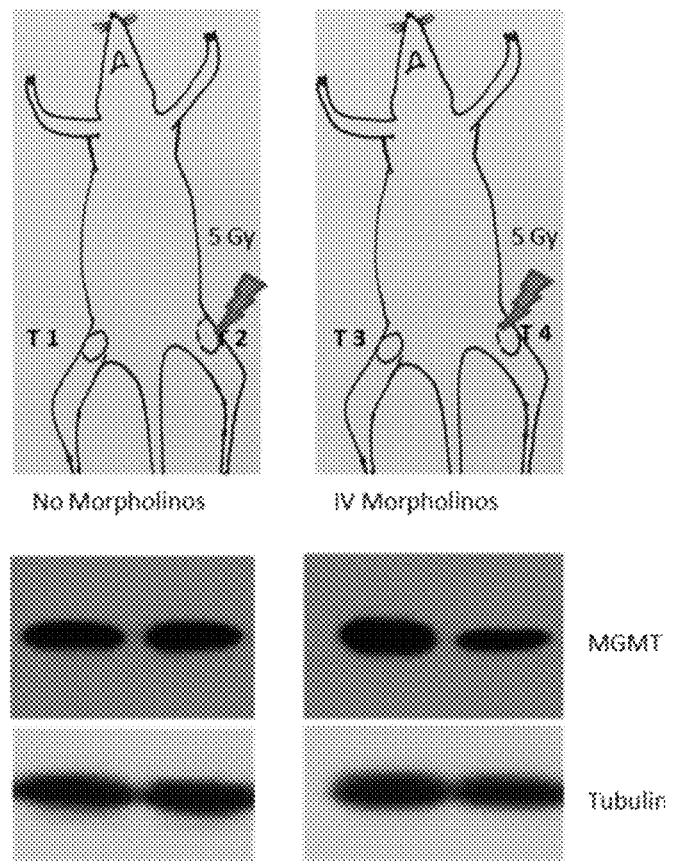
FIG. 4A is an illustration of an experimental procedure as well as an image of a Western blot that shows inhibition of MGMT expression in tumors grown in immunocompromised mice given a combination of morpholino oligonucleotides of SEQ ID NO: 1, SEQ ID NO: 2, and SEQ ID NO: 3 systemically as well as ionizing radiation directly to a tumor.
Figure 4B:
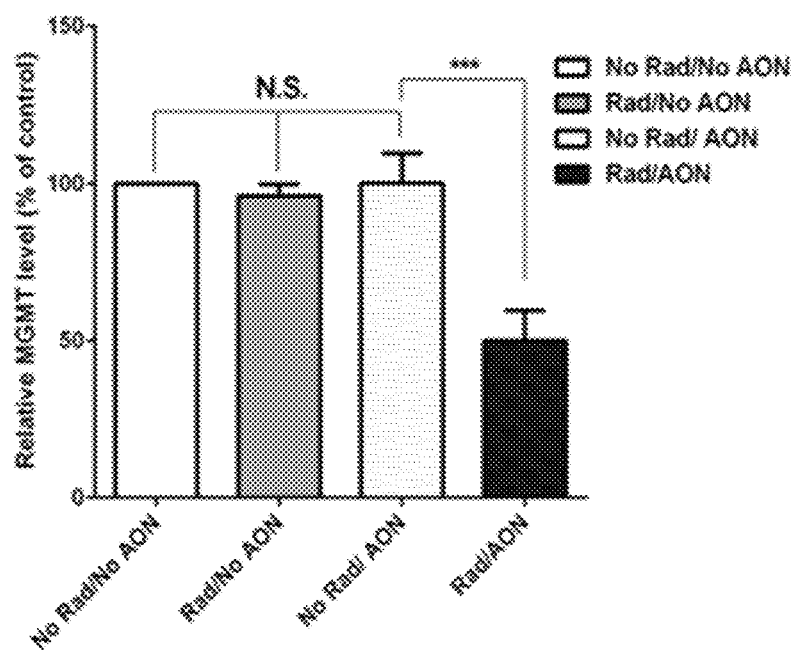
FIG. 4B is a graph summarizing the results seen in the Western blot.

Example 4—Treatment of Subcutaneous Xenograft Tumor Models with Local Radiation and Systemic Administration of AMON Due to the inconsistent growth of intracranial T98G cell lines, subcutaneous H460 NSCCL tumors in athymic nude rats were studied. $2.5 \times 10^7$ H460 cells were subcutaneously injected in each of their hind limbs of 6 animals. When the tumor reached 10 mm in diameter, a single dose of 5 Gy of ionizing radiation was delivered to the tumor field. AMON was administered intravenously (iv) through the femoral vein 24 hours after radiation. Tumors were harvested 3 days after exposure to AMONs. Western blots performed on the individual tumor cell lysates demonstrate that inhibition of MGMT expression was achieved in tumors that were radiated prior to iv administration of AMON. Inhibition of MGMT expression was not seen in control tumors that received systemic AMON but no radiation or those tumors that received radiation alone (FIGS. 4A and 4B).

MGMT-gene methylation status was tested in subcutaneous tumors to ascertain if either animal implantation, exposure to radiation or AMONs resulted in changes in methylation status that resulted in epigenetic silencing of the MGMT gene resulting in down regulation of MGMT. No significant changes in MGMT-gene methylation status was noted by pyrosequencing.

Example 5—Materials and Methods

Cell lines and reagents: Human T98G glioma, H460 and A549 non-small cell carcinoma cell lines were obtained from American Type Culture Collection (ATCC; Rockville, Md., USA) and cultured in suggested culture medium supplemented with in 10% FBS and 1% streptomycin/penicillin. Cells were maintained at 37° C. and in an atmosphere containing 5% CO2. Three MGMT antisense oligonucleotide sequences: SEQ ID NO: 1-5'-TTTCGTGCAGACCCTGCTCTT-3'; SEQ ID NO: 2-5'-TTCCATAACACCTGTCTGGTT-3'; SEQ ID NO: 3-5'-ATTCCTTCACGGCCAGTCCTT-3' and one non-specific control sequence: SEQ ID NO: 4-5'-CCTCTTACCTCAGTTACAATTTATA-3' were synthesized and purchased from Gene Tools, LLC (Philomath, Oreg., USA). Mouse anti-tubulin antibody (T9026) was purchased from Sigma (St. Louis, Mo., USA). Anti-MGMT (#2739), caspase 3 (#9662) and phospho-p53 (Ser15) (#9284) antibodies were purchased from Cell Signaling (Danvers, Mass., USA). Mouse anti-dynamin II (sc-166526) monoclonal antibody was purchased from Santa Cruz Biotechnology (Santa Cruz, Calif., USA).

Delivery of MGMT-morpholino in vitro into the cancer cells: Scrape delivery: $10^6$ cancer cells were seeded on a 10-cm culture plate. The culture plate was placed on a flat surface and the cells scraped off the surface with a sterile cell scraper. Different doses or combinations of MGMT-morpholinos were added to the cells. Scraped cell suspensions were pipetted up and down twice and transferred to another culture plate.

Transfection agent delivery: $10^6$ cancer cells were seeded in 10-cm culture plate. Cells were treated with transfection agent DharmaFECT (GE Dharmacon; Lafayette, Colo., USA) and MGMT-morpholinos mixture (1:1; v/v).

Radiation delivery: cell culture: $10^6$ cancer cells were exposed to different doses of radiation (0.5-12 Gy) at room temperature using a Philips gamma chamber (Philips Medical Systems, Andover, Mass.). After irradiation, cells were treated with mixtures of MGMT-morpholinos (SEQ ID NO: 1, SEQ ID NO: 2, SEQ ID NO: 3=1:1:1; v/v/v) at different time points and at a final concentration of 15 μM.

Delivery of MGMT-morpholino in vivo: Female (200-250 g) nude (rnu/rnu) and heterozygous (rnu/wt) rats were selected from the breeding colony maintained in the animal facility. For subcutaneous tumor model, a total of $2.5 \times 10^7$ cells were mixed (ratio 1:1; v/v) with Matrigel Basement Membrane Matrix (BD Biosciences, Bedford, Mass.), and the mixture was injected subcutaneously into both left and right hind legs. At d 7 after inoculation, right SQ tumor was exposed to single dose of radiation (5 Gy) with shielding the rest of body using a Philips gamma chamber (Philips Medical Systems, Andover, Mass.), and left SQ tumor of the same animal without radiation was served as control. A total of 30 mM MGMT-morpholinos SEQ ID NO: 1, SEQ ID NO: 2, SEQ ID NO: 3=1:1:1; v/v/v) was administered intravenously 24 h after irradiation. Tissues (SQ tumors, brain, liver, spleen and kidney) were harvested 3 days after morpholinos and subjected to further protein and DNA analysis.

Cell viability assay and western blot analyses: Cell viability and proliferation was measured using the WST-1 Proliferation Assay Kit from Chemicon International Inc. (Temecula, Calif.). Cells or tissues were harvested and then washed with ice-cold PBS twice before the addition of RIPA lysis buffer containing protease and phosphatase inhibitors. Protein concentration was quantified using the Bio-Rad method. Equal amounts of protein were loaded into each well and separated by 7.5 or 12% SDS-PAGE gel followed by transfer onto polyvinylidene difluoride membranes (Bio-Rad, Richmond, Calif.). Membranes were blocked using 5% nonfat dry milk or 2% bovine serum albumin (BSA) in PBS-T. The blots were then incubated with primary antibodies (1:200-1:1,000) overnight at 4° C. Secondary antibody (1:5,000; Cell signaling technology, Danvers, Mass.) was incubated for 2 h at room temperature. Immunoblots were developed using the chemiluminescence detection system (Thermo Scientific, Waltham, Mass.) according to the manufacturer's protocol and autoradiography. Quantification of immunoblotting signal of respective proteins was performed using UN-SCAN-IT Gel software (Silk Scientific, Inc., Orem, Utah).

Measurement of MGMT DNA methylation status: Subcutaneous xenograft tumor DNA was isolated using DNeasy Blood & Tissue Kit from Qiagen International (Germantown, Md., USA). In order to assure the quality and purity of DNA samples, the ratio of A260/A280 was determined and recorded samples was above 1.9. The percentage methylation status of MGMT DNA at CpG islands in samples were measured at using pyrosequening.

Statistical analysis: The results were expressed as mean±SEM, and the significance of the difference between the mean values of treated cells/animals and controls was corrected and determined by multiplying the p-value by the number of comparisons performed (n) according to Tukey's correction. For data analysis two-way ANOVA test was performed by comparing the different arms of treatment for the two variables. Significance was determined at the 5% level, two-sided. Statistical significance between treatment and control (or vehicle) group or any two other groups was indicated by * ($p<0.05$) or ** ($p<0.01$).

ADDITIONAL REFERENCES

The following references are hereby incorporated by reference in their entireties.

Morcos P A et al, Biotechniques 45, 613-618 (2008);
Fletcher S et al, Mol Ther 15, 1587-1592 (2007);
Cirak S et al, Lancet 378, 595-605 (2011);
Goemans N M et al, N Engl J Med 365, 1513-1522 (2011);
Agrawal S and Kandimalla E R, Mol Med today 6, 72-81 (2000);
Ball H A et al, Clin Rev Allergy Immunol 27, 207-217 (2004);
Stupp R et al, N Engl J Med 352, 987-996 (2005);
Hegi M E et al, N Engl J Med 352, 997-1003 (2005);
Ochs K et al, Cancer Res 5815-5824 (2000);
Kitange G J et al, Neuro Oncol 11, 281-291 (2009);
Bocangel D B et al, Clin Cancer Res 8, 2725-2734 (2002);
Karran P, Carcinogenesis 22, 1931-1937 (2001);
Kohsaka S et al, Cancer Lett 331, 68-75 (2013);
Goder A et al, Carcinogenesis 36, 817-831 (2015);
Kato T et al, Gene Ther 17, 1363-1371 (2010);
Wang T et al, Cancer Lett doi: 10.1016/j.canlet.2016.03.045 (2016);
Koo T and Wood M J, Hum Gene Ther 24, 479-488 (2013);
Tsujiuchi T et al, Am J Trans Res 6, 169-178 (2014);
Delaney G et al, Cancer 104, 1129-1137 (2005);
Maier P et al, Int J Mol Sci 17, E102. doi: 10.3390/ijms17010102 (2016);
Qian J et al, Cancer Res 65, 5493-5497 (2005);
Zhang M et al, Mol Ther 8, 21-28 (2003); and
Esteller M and Herman J G, Oncogene 23, 1-8 (2004).

The invention claimed is:

1. A method of treating a tumor, wherein said tumor overexpresses O-6-methylguanine-DNA methyltransferase (MGMT), in a subject, the method comprising:
   administering to the subject a composition comprising a morpholino oligonucleotide comprising SEQ ID NO: 1, SEQ ID NO: 2, or SEQ ID NO: 3, wherein the morpholino oligonucleotide is no more than 40 subunits in length, thereby treating the tumor.

2. The method of claim 1, further comprising administering a dose of ionizing radiation to the tumor.

3. The method of claim 2, wherein the dose of radiation is at least 1 Gy.

4. The method of claim 2, wherein the dose of radiation is at least 5 Gy.

5. The method of claim 2, wherein the dose of ionizing radiation is administered to the tumor prior to the administration of the composition to the subject.

6. The method of claim 5, wherein the dose of radiation is administered at least 24 hours prior to the administration of the composition.

7. The method of claim 1, further comprising administering temozoloamide to the subject.

8. The method of claim 1, wherein the tumor overexpressing MGMT is determined prior to administering to the subject the composition comprising a morpholino oligonucleotide comprising SEQ ID NO: 1, SEQ ID NO: 2, or SEQ ID NO: 3.

9. The method of claim 8, wherein determining that the tumor overexpresses MGMT comprises measuring expression of MGMT protein or measuring resistance to temozolomide in a sample of cells obtained from the tumor.

10. The method of claim 1, wherein the composition is administered intravenously.

11. A method of enhancing delivery of one or more morpholino oligonucleotides, the method comprising: administering to a subject with cancer a therapeutically effective amount of radiation prior to administering a therapeutically effective amount of the one or more morpholino oligonucleotides, wherein the one or more morpholino oligonucleotides comprise a sequence selected from SEQ ID NO: 1, SEQ ID NO: 2, or SEQ ID NO: 3, and wherein the morpholino oligonucleotide is no more than 40 subunits in length.

12. The method of claim 11, wherein the one or more morpholino oligonucleotides comprise a sequence selected from SEQ ID NO: 1, SEQ ID NO: 2, or SEQ ID NO: 3, and wherein the morpholino oligonucleotide is no more than 25 subunits in length.

13. The method of claim 11, wherein the one or more morpholino oligonucleotides consists of a sequence selected from SEQ ID NO: 1, SEQ ID NO: 2, or SEQ ID NO: 3.

14. The method of claim 11, wherein the morpholino oligonucleotide comprises SEQ ID NO: 1 and not SEQ ID NO: 2 and SEQ ID NO: 3; SEQ ID NO: 2 and not SEQ ID NO: 1 and SEQ ID NO: 3; SEQ ID NO: 3 and not SEQ ID NO: 1 and SEQ ID NO: 2; SEQ ID NO: 1 and SEQ ID NO: 2 and not SEQ ID NO: 3; SEQ ID NO: 1 and SEQ ID NO: 3 and not SEQ ID NO: 2; or SEQ ID NO: 2 and SEQ ID NO: 3 and not SEQ ID NO: 1.

15. The method of claim 11, wherein the dose of radiation is administered at least 24 hours prior to the administration of the one or more morpholino oligonucleotides.

16. The method of claim 1, wherein the morpholino oligonucleotide comprises SEQ ID NO: 1 and not SEQ ID NO: 2 and SEQ ID NO: 3; SEQ ID NO: 2 and not SEQ ID NO: 1 and SEQ ID NO: 3; SEQ ID NO: 3 and not SEQ ID NO: 1 and SEQ ID NO: 2; SEQ ID NO: 1 and SEQ ID NO:

2 and not SEQ ID NO: 3; SEQ ID NO: 1 and SEQ ID NO: 3 and not SEQ ID NO: 2; or SEQ ID NO: 2 and SEQ ID NO: 3 and not SEQ ID NO: 1, or SEQ ID NO: 1, SEQ ID NO: 2, and SEQ ID NO: 3.

17. The method of claim 1, wherein the morpholino oligonucleotides consists of a sequence selected from SEQ ID NO: 1, SEQ ID NO: 2, or SEQ ID NO: 3.

18. The method of claim 1, wherein the tumor is malignant.

19. The method of claim 1, wherein the tumor is in lungs or brain.

20. The method of claim 1, wherein the subject has a glioma or non-small cell lung cancer.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
tttcgtgcag accctgctct t          21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
ttccataaca cctgtctggt t          21

<210> SEQ ID NO 3
<211> LENGTH: 21
<212> TYPE: DNA
<213> ORGANISM: Artificial Sequence
<220> FEATURE:
<223> OTHER INFORMATION: Synthetic construct

<400> SEQUENCE: 3
attccttcac ggccagtcct t          21

<210> SEQ ID NO 4
<211> LENGTH: 25
<212> TYPE: DNA
<213> ORGANISM: Artificial sequence
<220> FEATURE:
<223> OTHER INFORMATION: Synthetic construct

<400> SEQUENCE: 4
cctcttacct cagttacaat ttata          25

<210> SEQ ID NO 5
<211> LENGTH: 207
<212> TYPE: PRT
<213> ORGANISM: Homo sapiens

<400> SEQUENCE: 5

Met Asp Lys Asp Cys Glu Met Lys Arg Thr Thr Leu Asp Ser Pro Leu
1               5                   10                  15

-continued

```
Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
            35                  40                  45

Pro Ala Ala Val Leu Gly Gly Pro Glu Pro Leu Met Gln Cys Thr Ala
 50                      55                  60

Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                 85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Lys Ala Ala Arg
            115                 120                 125

Ala Val Gly Gly Ala Met Arg Gly Asn Pro Val Pro Ile Leu Ile Pro
    130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
            195                 200                 205
```